(12) United States Patent
Vilozni

(10) Patent No.: US 6,508,772 B2
(45) Date of Patent: Jan. 21, 2003

(54) SPIROMETRY TEST AND ANALYSIS SYSTEM

(76) Inventor: Daphna Vilozni, Ha Odem 35/3, Hod Hasharon, 43540 (IL)

(*) Notice: Subject to any disclaimer, the term of this patent is extended or adjusted under 35 U.S.C. 154(b) by 71 days.

(21) Appl. No.: 09/747,978

(22) Filed: Dec. 27, 2000

(65) Prior Publication Data

US 2001/0003144 A1 Jun. 7, 2001

Related U.S. Application Data

(63) Continuation of application No. 09/330,596, filed on Jun. 11, 1999.

(30) Foreign Application Priority Data

Jun. 15, 1998 (DE) .......................................... 198 26 266

(51) Int. Cl.[7] ................................................. A61B 5/08
(52) U.S. Cl. ....................................................... 600/538
(58) Field of Search .................................. 600/538, 537, 600/533, 532, 531, 529, 539, 540

(56) References Cited

U.S. PATENT DOCUMENTS

| | | | |
|---|---|---|---|
| 3,635,214 A | | 1/1972 | Rand et al. |
| 3,857,385 A | | 12/1974 | Hampl |
| 3,896,792 A | * | 7/1975 | Vail et al. .................... 600/532 |
| 3,991,304 A | | 11/1976 | Hillsman |
| 4,241,739 A | * | 12/1980 | Elson ........................... 482/13 |
| 4,296,756 A | * | 10/1981 | Dunning et al. ............. 128/904 |
| 4,635,647 A | * | 1/1987 | Choksi .................... 128/200.14 |
| 4,809,706 A | | 3/1989 | Watson et al. |
| 4,984,158 A | | 1/1991 | Hillsman |
| 5,167,506 A | * | 12/1992 | Kilis et al. .................... 128/920 |
| 5,267,942 A | | 12/1993 | Saperston |
| 5,318,038 A | | 6/1994 | Jackson et al. |
| 5,333,106 A | | 7/1994 | Lanpher et al. |
| 5,555,891 A | | 9/1996 | Eisenfeld |
| 5,984,873 A | | 11/1999 | Crumb et al. |

FOREIGN PATENT DOCUMENTS

| | | |
|---|---|---|
| WO | WO 94/14374 | 12/1993 |
| WO | WO 97/01984 | 2/1996 |

OTHER PUBLICATIONS

Brochure from Sierra Biotechnology, "Biofeedback Incentive System("BIS")", www.sierrabiotech.com/bis.htm.

* cited by examiner

Primary Examiner—Max Hindenburg
Assistant Examiner—Navin Natnithithadha
(74) Attorney, Agent, or Firm—Mark H. Friedman

(57) ABSTRACT

A system for administering spirometry co-operative a test subject having limited comprehension capacity. The system includes a measuring sensor for measurement of a flow of air moving therethrough and one or more PID-controllers for evaluating the measurement of the flow of air. The system also includes a processor to co-ordinate actions of components to process data pertaining to evaluation of the measurement of the flow of air, and translate the measurement of the flow of air to clinically relevant parameters. Also included is one display visible to a person administering the spirometry to display clinically relevant parameters; a storage medium containing a pattern presentable to the test subject on an output medium to stimulate the test subject to cause air to flow through the sensor; and an output medium for presenting the pattern to the test subject; wherein the test subject, in a conscious effort to manipulate the pattern, repeatedly causes air to flow through the sensor; and wherein the pattern is designed to stimulate the test subject to cause the flow of air.

12 Claims, 1 Drawing Sheet

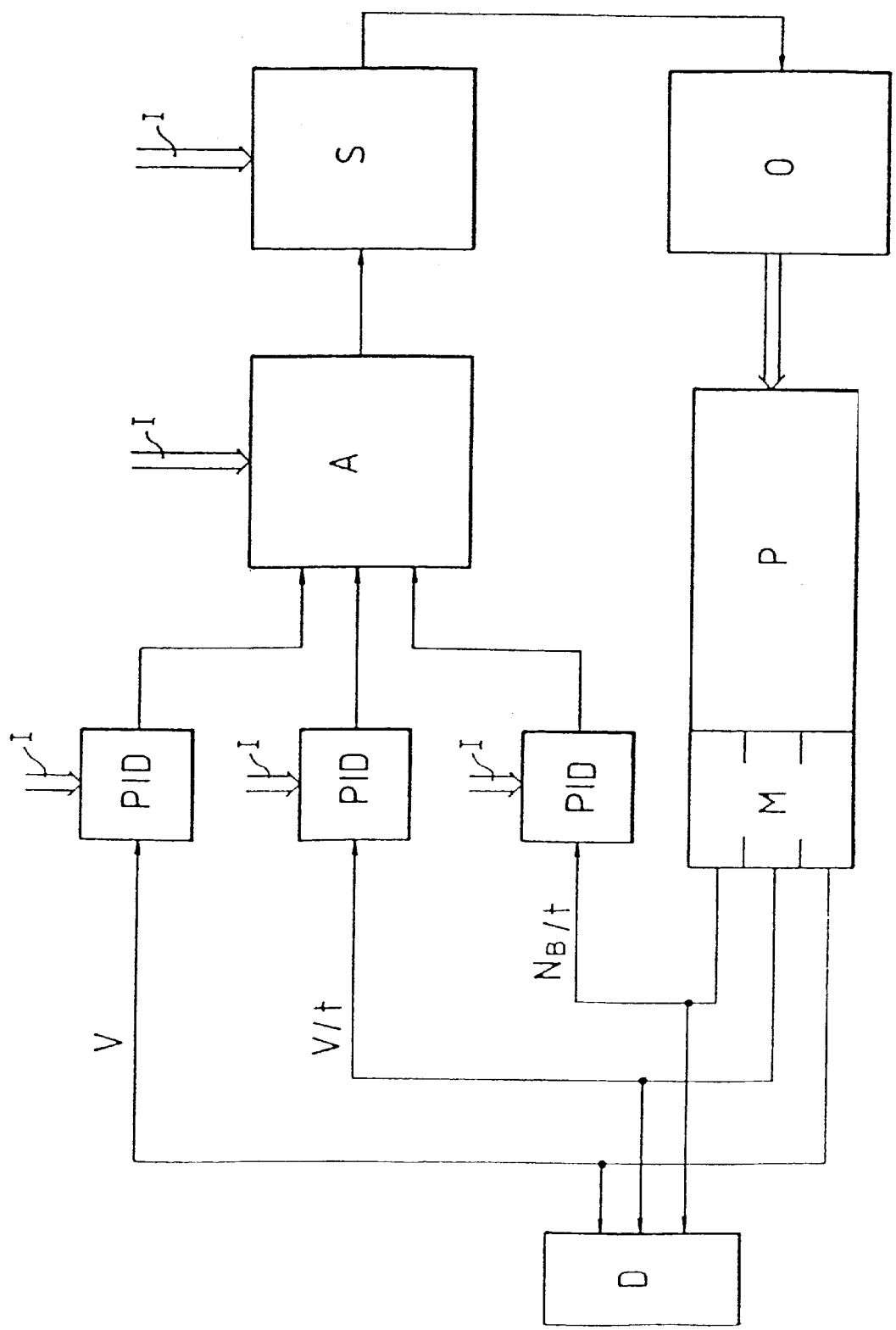
FIGURE

SPIROMETRY TEST AND ANALYSIS SYSTEM

This application is a continuation of U.S. patent application Ser. No. 09/330,596 filed Jun. 11, 1999 which claimed priority from German patent application DE 19826266.3 filed on Jun. 15, 1998.

FIELD AND BACKGROUND OF THE INVENTION

The present invention relates to a system for the test and analysis of lung functions or other breathing functions of people or animals, in particular pre-school children. The system is equipped with one or several spirometric sensors and with an output medium affecting the psyche and/or the nervous system of the subjects, which receives stimulating or animated displays or other data from a patterns source.

Spirometry is one of the cornerstones of pulmonary disease diagnostics. Its value was proven for children aged 6 and over. The patient, however, must comply with strict requirements. He must learn to take a breath as deep as possible, and upon order to blow out with all of his strength, until all air is expelled. This familiar spirometric system is designed for grownups, without paying attention to the apprehensions of children confronted by all this.

Pre-school children below 6 years of age are not normally conscious of breathing. In their instinctive respiratory processes they cannot distinguish between inhaling and exhaling. Pre-school children cannot be expected to respond when requested to take as deep a breath as possible and then to breath out with all their strength until as much air as possible is expelled. They can also hardly be persuaded to willingly collaborate in the procedures of spirometry and to undertake a considerable training effort beforehand, because they are too young for active cooperation of such extent. Apart from that, pre-school are frightened of the spirometer device.

A partial spirometry procedure is also known, which is based on subjective stimulation of inspiration or expiration in the patient. The patient is prompted by stimuli to a powerful and drawn-out expiration, but without regard for the preceding and succeeding intake of breath. This intake of breath, however is critical for correct measurement. The prompting is based on the patient's instinct, marked in particular among children, to draw a deep breath before the air is strongly blown out, for example in order to win a game (such as blowing out candles, jumping high, etc.). Such respiratory activities provide no certainty as to whether the child did or did not previously inhale the maximum quantity of air.

Accordingly, the present invention addresses the task of further developing breath-testing and analysis systems so that lung functions and breathing activities can also be reliably measured and analyzed in the case of pre-school children.

SUMMARY OF THE INVENTION

The proposed solution according to this invention is a test and analysis system of the kind mentioned in the introduction, in which the sensor or sensors are provided at their outputs with one or several filters which are controlled by the pattern source to which they are coupled on their output side and which permit further processing of the measured values included in the control signals, so that the date going out from the pattern source to the output medium depend on the input provided by breathing action or breathing state.

By means of this invention the pre-school may be unwittingly made to take a deep breath prior to the expiration to be measured, whereby the air quantity or the air volume inspired is also measured. The inventive idea consists in guiding breathing beings, in particular pre-school children or handicapped children, to perform correct lung-function activities by exposing them to an effective output medium, for example displaying animated graphics. Inspiratory air volume, volume flow and respiratory disturbances are registered by the sensors and in turn affect the filter or filters of the output medium, such as the animated pictures on a screen, which the pre-school child follows in the course of measurement. The patterns displayed on the output medium before the pre-school child or other living being, such as moving figures on a screen, may be configured in known manner so that the respiration of the child is positively affected. A particular advantage can be realized if the child or other living being is presented with stimuli on the output medium, for instance in the form of animated graphics, which are embedded in a story of suitable context these being interactively controlled by the respiration of the child via the sensors, filters and eventually the associated computer. The stories provided on the output medium may also be of educational value for the child.

Another advantage achieved by the invention is that a complete spiromteric process is realized, since not only the expiration but also the inspiration is recorded. This provided a basis for the analysis of tidal respiration and the performance of a bronchial stimulation test.

It would be useful to hook up a processor to the filter outputs. Such processor would control a storage medium serving as the source for the patterns provided to the output medium. The stored data may contain patterns which correspond to stimuli or animations rooted in the children's world. It would thus be possible to make pre-school children take separate respiratory activity. The games may require the solution of problems of different degree of difficulty, whereby the solution of such a problem is suitable rewarded. The stimulating patterns may be arranged to form a story with due regard for the limited concentration time of the child, which would facilitate the collaboration required for bronchial stimulation.

In order to reduce the terrifying aspects of the analysis and test system and enhance the participation and readiness to cooperate of the patient, it is useful in the case of pre-school children to construct the system sub-assemblies (mouthpieces, lung tachographs, etc.) so as to suit the stature, strength and spirit of pre-school children.

BRIEF DESCRIPTION OF THE DRAWINGS

Other characteristics, details, advantages and affects based on the invention will become apparent from the following description of a preferred embodiment of the invention, as well as from the FIGURE which shows a block diagram of an example of the test and analysis according to the invention.

DESCRIPTION OF THE PREFERRED EMBODIMENT

The respiration of a person under test P, in particular a pre-school child, is registered by the measuring sensors M which provide the inspiratory and expiratory air volume V the bi-directional airflow V/t and the breathing frequency $N_B/t$ (number of respirations $N_B$ per time unit t). The measured values, V, V/t, $N_B/t$ are transferred to separate filters, which in the example shown in the drawing consist of PID-controllers.(Proportional Integral Derivative controllers) These filters or controllers carry out an evaluation of the aforementioned measured values which originate with the person under test P, and at the same time form the control section of a closed control loop. It is useful to bring out the results of these measurements in parallel also to a display D, on which it is also possible to display other parameters in real time on a suitable scale. In particular, forecast values and the values of preceding measurements may be shown on the display D jointly with the present measurements.

The outputs of the PID filters, each assigned to a separate measured quantity, are led to a common processor A. This may, for example, be configured as an adder of the measurement results evaluated by the PID filters. Its output controls a storage medium holding stimulation, animation or other data patterns, which are in the first place tailored for pre-school children. The control link may for example lead through the address inputs of the storage medium, when these are digital. It is also useful to have the storage medium provided with an extra input I, through which external data patterns may be entered or patterns existing in the storage medium may be deleted. The contents of the storage medium S, which is the data patterns, are led out to an output medium O, such as a screen, which is visually perceived by the person under test. In addition, the output unit can also be, provided with other interfaces of acoustic nature (such as loudspeakers). The patterns presented to the person under test P which are sent out from the storage medium S to the output unit O, served to animate and stimulate this person's psyche and nervous system in accordance with the diagnostic purpose, whereby the natures of this person's respiration and hence the measured values V, V/t, $N_B/t$ may be influenced in individually-targeted manner. The output medium O provides a sort of adjustment of the control loop, whereby the PID filters with the processor A and the storage medium S form the controller. This controller can have its parameters adjusted before the control operation by means of the inputs I leading to the PID filters, the processor A and the storage medium S, or also in the course of the control operation to provide adaptation to changing circumstances.

The picture shown on the output medium O can be made familiar to the pre-school child from his or her real environment. The child can interactively change the picture or remodel it by means of the mouthpiece or a lung tachograph. Each respiratory activity, including inspiration as well as expiration, causes a predetermined movement of the picture element. The corresponding pictorial information is stored beforehand in the storage medium S. In this way the child may be presented with problems, for example in the form of computer games, whereby attainment of a goal or solution of a problem is rewarded or recognized. Each game deposited in the storage medium S has multiple degrees of difficulty. The games are so structured as to serve the purpose of the lung or respiration test desired and at the same time take account of the concentration ability of the child. A particular advantage is realized by having each such game structured as "a short story" with a surprising ending. The associated software should preferably be made compatible with the resident operating systems and hospital data banks.

While the invention has been described in detail for the purpose of illustration, it is to be understood and appreciated that such detail is solely and purely for the purpose of example and that many other variations, modifications and applications of the invention can be made by those skilled in the art without departing from the spirit and scope of the invention.

What is claimed:

1. An improved system for administering spirometry to a test subject that is co-operative although of limited comprehension capacity, the system comprising:
    (a) a measuring sensor designed and configured for measurement of a flow of air moving therethrough;
    (b) at least one PID-controller for evaluating said measurement of said flow of air;
    (c) a processor designed and configured to:
        (i) co-ordinate actions of components comprising the system;
        (ii) process data pertaining to evaluating said measurement of said flow of air;
        (iii) translate said measurement of said flow of air to clinically relevant parameters;
    (d) a display visible to a person administering the spirometry, said display displaying said clinically relevant parameters;
    (e) a storage medium containing a game presentable to the test subject of limited comprehension capacity on an output medium, said game serving to stimulate the test subject of limited comprehension capacity to cause air to flow through said sensor; and
    (f) said output medium for presenting said game to the test subject of limited comprehension capacity;
    wherein the test subject of limited comprehension capacity, in a conscious effort to manipulate said game, repeatedly causes air to flow through said sensor; and
    wherein said game is designed to stimulate the test subject of limited comprehension capacity to cause said flow of air.

2. The system of claim 1, wherein said measurement includes at least one measurement selected from the group consisting of volume (V), bi-directional airflow V/t, and breathing frequency $N_B$ /t.

3. The system of claim 2, wherein said processor includes an adder capable of calculating a sum of said evaluations from at least two of said at least one PID controllers.

4. The system of claim 2 wherein said PID-controllers function as band-pass filters.

5. The system of claim 4, wherein said output medium is selected from the group consisting of a visual display and an audio display.

6. The system of claim 1, wherein said effort required to manipulate said game is adjusted according a capacity of the test subject of limited comprehension capacity.

7. An improved method for administering spirometry to a test subject that is co-operative although of limited comprehension capacity, the method comprising the steps of:
    (a) measuring a flow of air moving through a sensor and generating a measurement thereof;
    (b) evaluating said measurement of said flow of air by means of at least one PID-controller for;
    (c) employing a processor to perform at least one function selected from the group consisting of:
        (i) co-ordinating actions of said sensor, said at least one PID controller, a display, a storage medium and an output medium;
        (ii) processing data pertaining to evaluating said measurement of said flow of air;
        (iii) translating said measurement of said flow of air to clinically relevant parameters;
    (d) displaying on said display said clinically relevant parameters to a person administering the spirometry;
    (e) providing in a storage medium a game presentable to the test subject of limited comprehension capacity on said output medium, said game serving to stimulate the test subject of limited comprehension capacity to cause air to flow through said sensor; and (f) presenting said game to the test subject of limited comprehension capacity via said output medium;

wherein the test subject of limited comprehension capacity, in a conscious effort to manipulate said game, repeatedly causes air to flow through said sensor; and wherein said game is designed to stimulate the test subject of limited comprehension capacity to cause movement of said flow of air.

8. The method of claim 7, wherein said measuring includes measuring of at least one measuring at least one parameter selected from the group consisting of volume (V), bi-directional airflow V/t, and breathing frequency $N_B$ /t.

9. The method of claim 7, wherein said processor is further capable of calculating a sum of said evaluations from at least two of said at least one PID controllers.

10. The method of claim 7, wherein band pass filtering is performed by said PID-controllers.

11. The method of claim 7, wherein said step of presenting said game employs an output medium selected from the group consisting of a visual display and an audio display.

12. The method of claim 7, comprising the additional step of adjusting said effort required to manipulate said game according a capacity of the test subject of limited comprehension capacity.

* * * * *